(12) United States Patent
Solem

(10) Patent No.: US 6,585,650 B1
(45) Date of Patent: Jul. 1, 2003

(54) METHOD AND SYSTEM FOR BYPASSING AN ARTERY BLOCK

(75) Inventor: Jan Otto Solem, Bjärred (SE)

(73) Assignee: Jomed N.V., Ulestraten (NL)

( * ) Notice: Subject to any disclaimer, the term of this patent is extended or adjusted under 35 U.S.C. 154(b) by 0 days.

(21) Appl. No.: 09/562,027

(22) Filed: May 1, 2000

(30) Foreign Application Priority Data

Mar. 20, 2000 (SE) ................................ 0000900

(51) Int. Cl.$^7$ .................................. A61B 8/00
(52) U.S. Cl. ..................... 600/438; 606/159; 606/7
(58) Field of Search ................. 606/159, 184; 604/96; 623/1, 1.11, 12.11; 128/898; 600/438

(56) References Cited

U.S. PATENT DOCUMENTS

| | | |
|---|---|---|
| 5,830,222 A | 11/1998 | Makower |
| 5,976,178 A | 11/1999 | Goldstein et al. |
| 5,989,276 A | 11/1999 | Houser et al. |
| 6,068,638 A | 5/2000 | Makower |
| 6,081,738 A | 6/2000 | Hinohara et al. |
| 6,241,741 B1 * | 6/2001 | Duhaylongsod et al. .... 606/153 |
| 6,266,550 B1 * | 7/2001 | Selmon et al. ............. 600/407 |
| 6,387,119 B2 * | 5/2002 | Wolf et al. ................ 128/898 |

FOREIGN PATENT DOCUMENTS

| | | |
|---|---|---|
| WO | WO 97/13463 | 4/1997 |
| WO | WO 99/35978 | 7/1999 |
| WO | WO 99/35980 | 7/1999 |

* cited by examiner

Primary Examiner—Francis J. Jaworski
Assistant Examiner—Maulin Patel
(74) Attorney, Agent, or Firm—Browdy and Neimark, P.L.L.C.

(57) ABSTRACT

A catheter system for use in bypassing a block in an artery comprises four components. These components are an arterial catheter, an intravenous ultrasound catheter, a guide wire system, and finally a covered stent used as graft. The bypassing of the block in the artery which extends along a vein comprises the steps of forming a first connection between said artery and said vein proximal to the block in the artery, forming a second connection between said artery and said vein distal to the block in the artery, introducing a covered stent through said artery proximal to the block therein, through said first connection into said vein, via said vein to and through said second connection, and into said artery distal to the block therein, such that a proximal end of the covered stent is positioned in the artery proximal to the block therein and a distal end of the covered stent is positioned in the artery distal to the block therein, and fixing the proximal and distal ends of the covered stent within the artery.

42 Claims, 11 Drawing Sheets

METHOD AND SYSTEM FOR BYPASSING AN ARTERY BLOCK

BACKGROUND OF THE INVENTION

The present invention relates to a method of bypassing a block or an occlusion in an artery. The invention also relates to a catheter system for use in bypassing such a block or occlusion in an artery.

Coronary artery disease is the most common cause of death today. Apart from that, more people suffer from pain and discomfort from the disease than those who die. The cause of these problems is mostly localized blocks, also called stenosis, in the arteries that support the heart muscle with energy and oxygen. Pain or death of muscle tissue occurs when this support ceases or is insufficient.

Today almost all incomplete blocks in these arteries are treated by means of dilating balloons that are placed across the blocks and inflated, whereby the blocked site of the vessel may be widened and the arterial fresh blood may pass again. The irregularities that occur in the vessel wall after such percutaneous transarterial coronary angioplasty (PTCA) are today secured and controlled by means of a so-called stent, e.g. a metal cylinder that also is dilated in the same way when in place over the treated area of the vessel, whereby it is pressed against the vessel wall and will remain there as a support.

The vessel has, however, to be open through the narrow part to enable treatment of the block with a balloon. This is the case for about half the population of the coronary deceased people. The other half will have to undergo coronary artery bypass surgery. During this procedure the block in the vessel is shunted (or bypassed) by means of a conduit usually taken from the person himself, whereby fresh blood is guided from another artery upstream through a new passage past the blocked area into the distal part of such a deceased vessel.

Every year about one million people in the Western World undergo the balloon treatment and another million people have coronary artery bypass surgery. The surgery usually involves the use of extra-corporeal circulation, the heart and lung machine, full anesthesia, open chest and long recovery and rehabilitation periods. After having a PTCA, however, the patient will leave the hospital the next day since no anesthesia was necessary and also no major surgery was done.

According to U.S. Pat. No. 5,830,222 of Joshua Makower, a percutaneous revascularization is obtained by arterializing a distal part of a vein, whereby blood flows from a blocked artery and in a retrograde fashion in this distal part of the vein, or by simply using a portion of the vein as a bypass graft, whereby the part of the vein distal to this portion is cut off. Thus, in both these cases the ordinary function of the distal part of the vein is blocked, which may lead to problems as regards blood drainage from the area of the cut-off distal part of the vein.

SUMMARY OF THE INVENTION

A main object of the present invention is to provide a new possibility for many of the patients that undergo surgery today of being treated with a similar method as the PTCA, i.e. awake and with no anesthesia and no major surgery even if the artery in question is totally blocked.

A further object of the invention is to provide such surgery without eliminating the function of parts of veins distal to the block or occlusion in an artery.

This object is attained on the basis of the anatomical peculiarity that most of the arteries in the human body are in very close proximity to a vein draining blood from the same area as the artery supports.

In the case of the heart, the artery and the vein usually are so close to each other that contact is present. Moreover, it is very easy to get access to the venous system of the heart since the coronary sinus, the endpoint of the venous drainage from the heart, is easily accessible in the right atrium, only about 20 cm from the patient's neck and is connected to the big jugular vein in the neck.

Further, an observation that is of great importance for the present invention is the fact that the veins are usually much greater in diameter than the arteries. According to the invention, a covered stent of smaller diameter than the vein is used to bypass the block in the adjacent artery without blocking the flow in the vein itself. Thus the covered stent is positioned in the vein and its ends are connected to the adjacent artery on either side of the block therein.

In this context, the covered stent is essentially equivalent to a vascular graft or a stented vascular graft. In this application, a covered stent is to be understood as a vessel which is flexible, may be dilated and will maintain its dilated shape.

More precisely, the above objects of the invention are achieved by a method and a catheter system as defined in the independent claims. Preferred embodiments of the invention are defined in the dependent claims.

Thus, a method of bypassing a block in an artery which extends along a vein, comprises the steps of forming a first connection between said artery and said vein proximal to the block in the artery, forming a second connection between said artery and said vein distal to the block in the artery, introducing a covered stent through said artery proximal to the block therein, through said first connection into said vein, via said vein to and through said second connection, and into said artery distal to the block therein, such that a proximal end of the covered stent is positioned in the artery proximal to the block therein and a distal end of the covered stent is positioned in the artery distal to the block therein, and fixing the proximal and distal ends of the covered stent within the artery.

The forming of said first connection preferably comprises introducing a first catheter through the artery, said first catheter having a lateral opening at a distal end thereof, positioning said lateral opening so as to face said vein proximal to said block, introducing a first therapeutic wire through said first catheter, said first therapeutic wire having an active distal end, advancing the distal end of the first therapeutic wire through the lateral opening of said first catheter, out of the artery and into the vein, thereby forming the first connection.

The forming of the second connection preferably comprises introducing a second catheter through the vein, said second catheter having a lateral opening at a distal end thereof, positioning said lateral opening so as to face said artery distal to said block, introducing a second therapeutic wire through said second catheter, said second therapeutic wire having an active distal end, advancing the distal end of the second therapeutic wire through the lateral opening of said second catheter, out of the vein and into the artery distal to said block, thereby forming the second connection.

It is most preferable to include a step of catching the distal end of the first therapeutic wire and retracting it through the vein, the first therapeutic wire then extending through the artery proximal to the block, through the first connection and through the vein proximal to the block. As a result, proximal ends of the first and second therapeutic wires extending through the vein may be joined to each other, preferably outside the body, and the first therapeutic wire may be retracted through the artery, such that the second therapeutic wire extends from the artery distal to the block, through the second connection, via the vein to and through the first connection and into the artery proximal to the block, and finally along the artery proximal of the block.

Concluding, the covered stent could be introduced on the second therapeutic wire for bypassing the block and be fixed by dilation of the stent, preferably by means of a balloon.

It should be noted that the stent should be dilated to a diameter which is smaller than the diameter of the vein enclosing part of the covered stent.

In order to position the lateral opening of said first catheter so as to face said vein proximal to said block, a detector is introduced into the vein for detecting the position of the lateral opening in the first catheter. This detector is used first to detect the positions of the block in the artery and then to detect the position of the lateral opening in the first catheter.

The position detector may be an ultrasonic transducer, which is used to detect the position of an ultra-sound reflecting marking, provided on the first catheter in a predetermined relation to the lateral opening at the distal end thereof.

The positioning of the lateral opening of said second catheter so as to face said artery distal to said block may comprise providing a detector on the second catheter and close to the lateral opening thereof for detecting the position of the artery distal to the block.

Preferably, an ultrasonic transducer is used as position detector on the second catheter.

The ultrasound transducers may have the capacity of viewing in a more limited sector and/or 360° around the catheter. Further, the ultrasound transducer should be capable of penetrating and depicting structure outside the vessel of its own location, i.e. beyond the wall of that vessel and into adjacent tissue or vessels.

According to the invention, a method of bypassing a block in an artery which extends along a vein, may alternatively comprise the steps of providing a covered stent having a proximal end and a distal end, positioning the covered stent within said vein having its proximal end introduced into said artery proximal to the block therein and having its distal end introduced into said artery distal to the block therein, connecting the proximal end of the covered stent to the artery proximal to the block, and connecting the distal end of the covered stent to the artery distal to the block.

The covered stent used should preferably have a diameter which is smaller than the diameter of the vein enclosing part of the covered stent.

The catheter system of the invention for use in bypassing a block in an artery and performing the above method preferably comprises four components. These components are an arterial catheter, an intravenous catheter, a guide-wire system, and finally a covered stent used as graft.

According to the invention, the catheter system comprises an arterial catheter for introduction into said artery, a distal end of the arterial catheter having a lateral opening to be positioned proximal to the block in said artery, and a wire having a cutting tip at a distal end thereof, said wire being advanceable through the arterial catheter so as to project the cutting tip out through the lateral opening at the distal end of the arterial catheter and thereby laterally out through a wall of the artery.

The arterial catheter may have a flap connected to a distal edge of the lateral opening, said flap being inclined towards the opposite side of the arterial catheter and having a free end proximal of said distal edge. Preferably, the flap is flexible to a position substantially covering the lateral opening of the arterial catheter.

The catheter system may use ultrasound technique for the determination of position. Then, an ultrasound reflecting material is fixed in a predetermined position relative to the lateral opening of the arterial catheter. Preferably, this ultrasound reflecting material at least partly encircles the lateral opening of the arterial catheter.

The catheter system may further comprise an ultrasound catheter for introduction into a vein extending along said artery, which ultrasound catheter may comprise an ultrasonic transducer for determining the position of the block in the artery and for monitoring a positioning of the lateral opening of the arterial catheter when introduced into said artery so as to face the vein.

Preferably, the ultrasonic transducer is directed laterally substantially in the direction of the laterally directed distal opening and positioned distal to the laterally directed opening.

It should be noted that the invention may be used for any pair of an artery and an adjacent vein in the body and not exclusively for such pairs in the heart.

DESCRIPTION OF PREFERRED EMBODIMENTS

As stated above, it is an anatomical peculiarity that most of the arteries in the human body are in very close proximity to a vein draining blood from the same area as the artery supports. Also, the veins are usually much greater in diameter than the arteries, an observation that is of great importance for the present invention, since the present invention uses such a wide vein as a medium to navigate in for the proper placement of a covered stent and also lends some of its space (diameter) for passing a new conduit past the block in the adjacent artery without block the flow in the vein itself.

Figure 1:
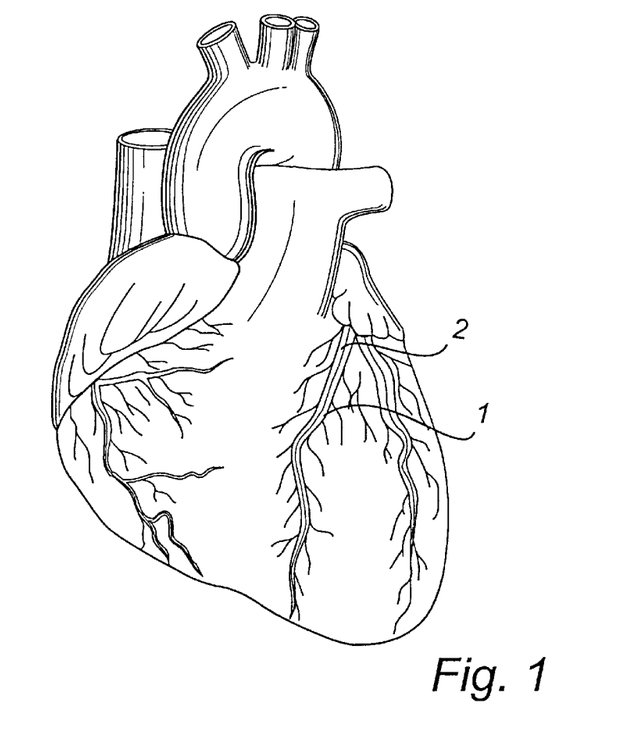
FIG. 1 illustrates the anatomy of a human heart.

FIG. 1 shows the anatomy of the heart seen from the front and shows the close relationship between arteries 1 and veins 2. This close relationship exists also between the veins and the arteries on the backside of the heart and further in many peripheral positions in the body.

Figure 2:
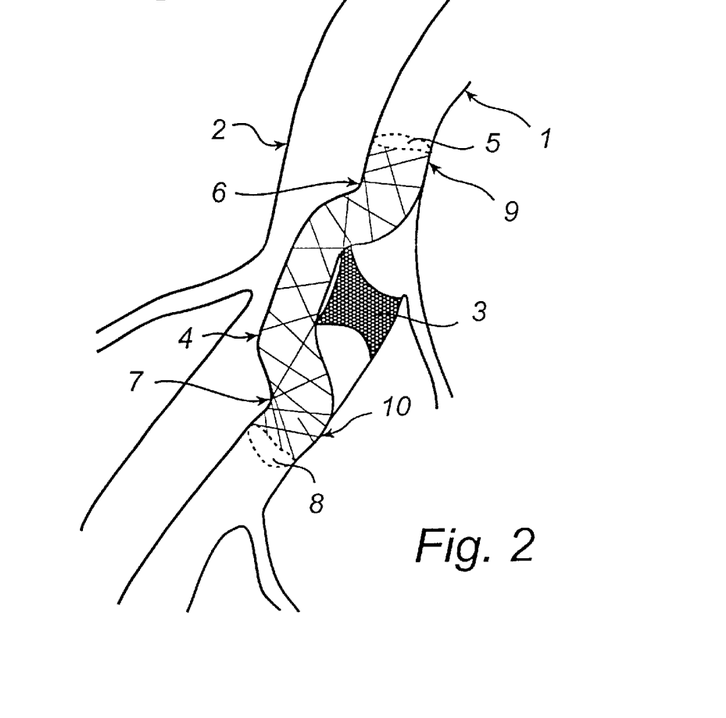
FIG. 2 illustrates a finished coupling according to the present invention bypassing a block in an artery of the heart.
Figure 3:
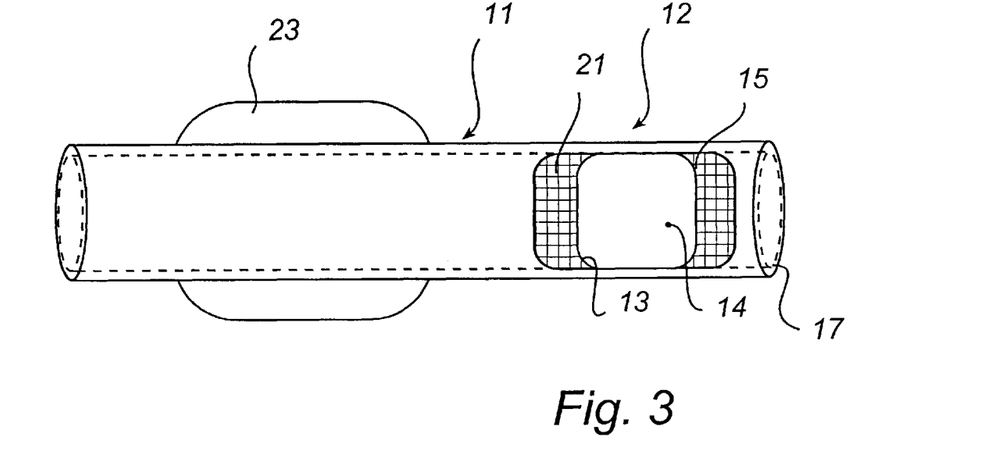
FIG. 3 is a top plan view of a distal part of an embodiment of a first catheter designed as an arterial catheter according to the invention for use in a method of bypassing a block in an artery according to the present invention.

FIG. 2 illustrates a finished coupling bypassing a block 3 in an artery 1 of the heart. This coupling comprises a covered stent 4, which extends from a first point 5 within the artery upstream of the block 3, via a connection 6 out from the artery 1 into an adjacent vein 2, within the vein 2 past the block 3 in the adjacent artery 1, via a connection 7 out from the vein 2 and back into the adjacent artery 1, and to a second point 8 within the artery 1 downstream of the block 3. A proximal end 9 of the covered stent 4 is fixed in the artery 1 at least at the first point 5, and a distal end 10 of the covered stent 4 is fixed in the artery 1 at least at the second point 8. The cross-sectional area of the covered stent 4 is smaller than the cross-sectional area of the vein 2, whereby the vein 2 still is capable of letting a stream of blood flow back towards the right atrium past the block 3 in the adjacent artery 1. At the same time, a stream of blood can pass from the heart through the artery 1 to the covered stent 4 upstream of the block 3 and via the covered stent 4 to the artery 1 downstream of the block 3, and then further out into the ramification of the artery 1.

FIGS. 3–15 illustrate preferred embodiments of an instrumental system that may be used to perform the method according to the present invention, whereby the finished connection illustrated in FIG. 2 may be obtained. The most essential parts of this system are an arterial catheter and an intravenous catheter, illustrated in FIGS. 3–13.

Figure 14:
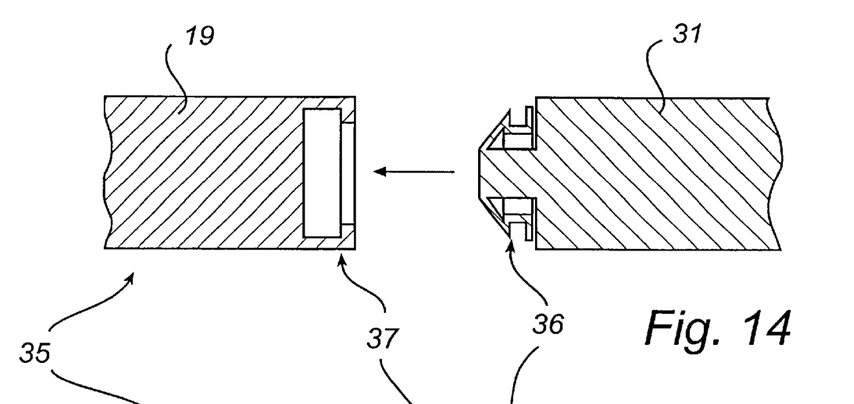
FIGS. 14 and 15 illustrate a lock mechanism for connecting therapeutic wires or part thereof according to the present invention.
Figure 15:
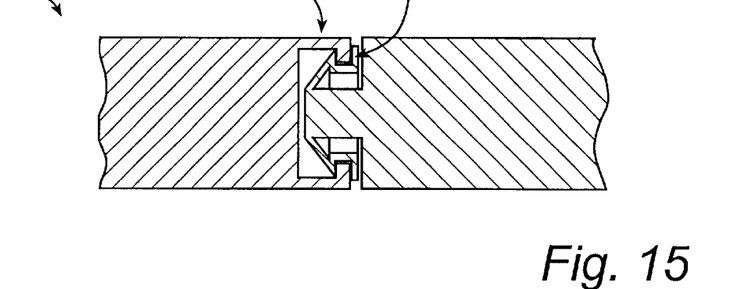

The preferred embodiment of the instrumental system of the present invention further comprises a wire system including conventional guide wires and therapeutic wires having lock mechanisms illustrated in FIGS. 14 and 15.

FIGS. 3–7 illustrate a first embodiment of an arterial catheter 11, which at a distal end 12 has a lateral opening 13. A flap or tongue 14 is connected to the catheter 11 at a distal edge 15 of the lateral opening 13. This flap 14 is inclined towards the opposite side of the arterial catheter 11 and has a free end 16 proximal to the distal edge 15.

Consequently, a wire being guided through the arterial catheter towards the distal end 12 will be deflected by the flap 14 to project out through the lateral opening 13.

Figure 5:
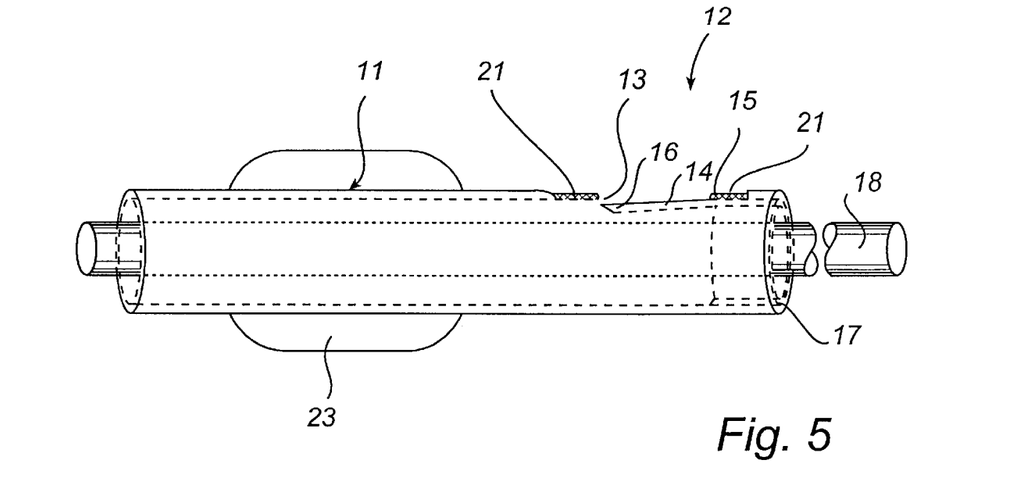
FIG. 5 is an elevation view of the first catheter shown in FIG. 3 and also illustrates a wire introduced through a distal end opening of the catheter.

The arterial catheter 11 also has an opening 17 axially at its distal end, and the flap 14 preferably is flexible to a position substantially covering the lateral opening 13. As a result, a wire 18 may be introduced into the arterial catheter 11, or vice versa, via the opening 17 and past the flap 14, which then will deflect towards the lateral opening 13, as shown in FIG. 5.

When using the arterial catheter 11 it is inserted into an artery, e.g. the artery 1 in FIG. 2, such that the lateral opening 13 is positioned opposite to the adjacent vein 2 directly upstream of the block 3. Then a wire 19 having a cutting tip 20 is inserted through the arterial catheter 11 such that the cutting tip 20 will be deflected laterally by the flap 14 out of the lateral opening 13, through the wall of the artery 1 and the wall of the adjacent vein 2 into this vein 2. The cutting or active end or tip 20 is capable of cutting through the wall of a blood vessel and may use radio frequency energy, laser energy, or a sharp end.

In order to be able to perform this operation, it must be possible to determine the rotational position of the lateral opening 13 at the distal end 12 of the arterial catheter 11 within an artery into which the arterial catheter 11 is inserted. Preferably, this is attained by attaching a rotational position indicator 21 to the distal end of the arterial catheter and introducing a detector 22 (cf. FIGS. 9–13) through the adjacent vein to a position close to the rotational position indicator 21, this detector 22 being sensitive to the rotational position of the rotational position indicator 21.

Further, a balloon 23 is provided at the distal part 12 of the artery catheter 11. The balloon 23 is inflated when the rotational position of the distal opening 13 of the artery catheter 11 is opposite to the adjacent vein, as determined by the rotational position detector 22. Consequently, the position of the artery catheter 11 is fixed relative to the adjacent vein.

As a preferred example, the rotational position indicator 21 may be an ultrasound reflecting material provided non-concentrically on the arterial catheter 11 near the distal opening 13, e.g. so as to at least cover part of the edge around the distal opening 13. In this case, the detector 22 should comprise an ultrasound head, which is able to detect the rotational position of the arterial catheter 11.

Other types of indicators and detectors, such as a magnetic indicator and a magnetic detector, are of course possible. Each type of indicator and detector may be used separately or in combination with another type of indicator or detector.

It is also possible that the material of the arterial catheter 11 is such as to enable a detecting of the rotational position of the distal end 12 thereof as a consequence of the presence of the opening 13 and/or the flap 14 which themselves are non-concentric in relation to a central axis of the arterial catheter 11. Thus, this would eliminate any extra material being applied to the distal end 12 of the arterial catheter 11 to make it indicative of its rotational position.

Figure 4:
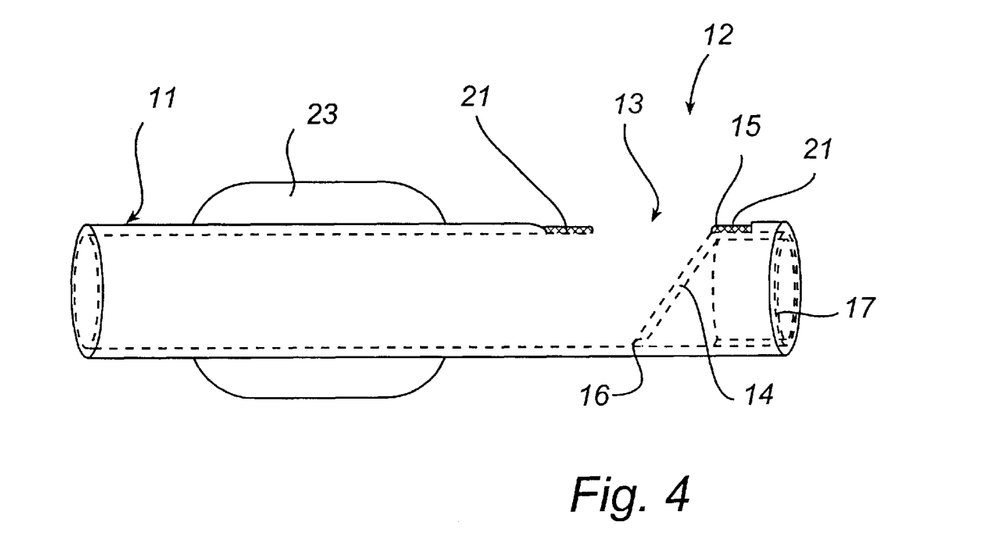
FIG. 4 is a longitudinal sectional view of the first catheter shown in Fig. 3.
Figure 6:
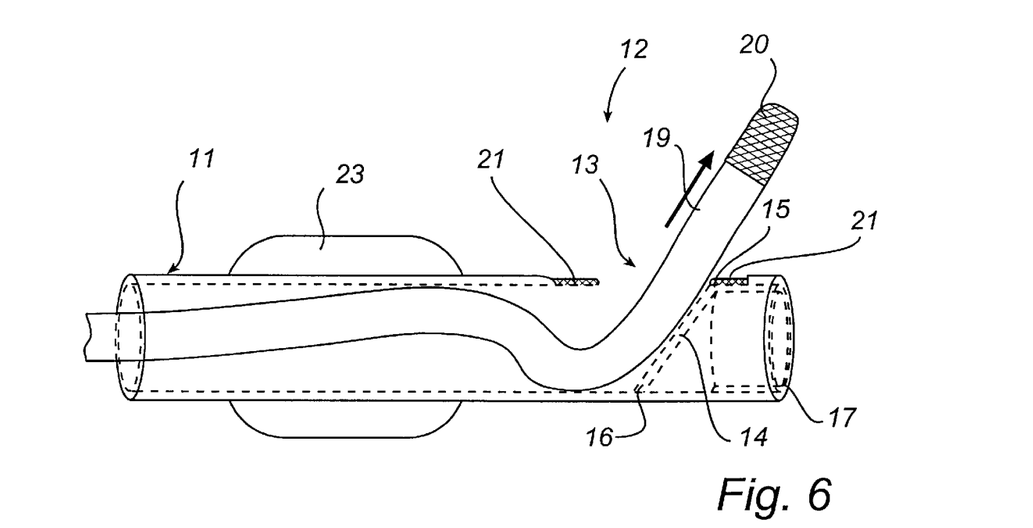
FIG. 6 is an elevation view of the first catheter shown in FIG. 3 and also illustrates a wire having an active head introduced from the proximal end of the catheter and out of a lateral opening of the catheter.
Figure 7:
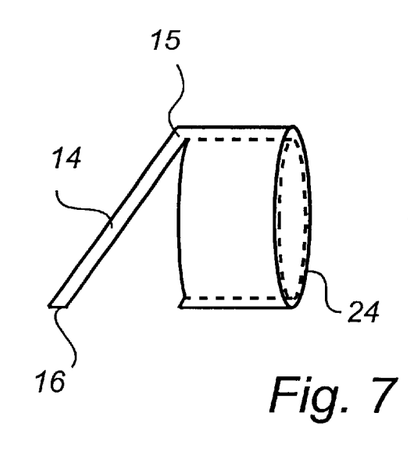
FIGS. 7 and 8 illustrate two positions of a flap device of the first catheter.
Figure 8:
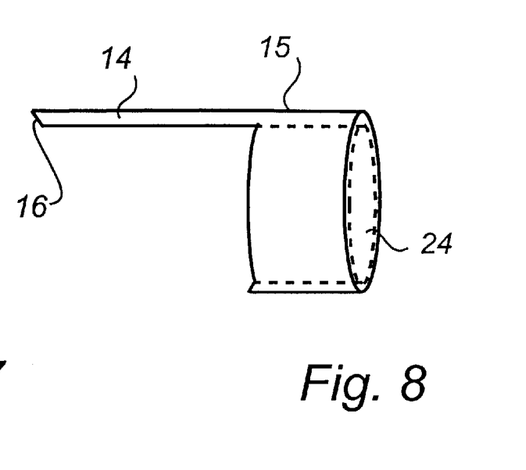

FIGS. 7 and 8 illustrate an exemplary design of the flap 14. More precisely, the flap 14 is fixed to a ring 24 which may be inserted into the opening 17 of the catheter 11 and fixed therein adjacent to the opening 13, as illustrated in FIGS. 4–6. FIG. 7 shows the flap 14 in its inclined position, and FIG. 8 shows the flap 14 in its position flexed upward towards the opening 13. Other embodiments of the flap 14, e.g. a flap integrated in the catheter, are obvious to the man skilled in the art.

Figure 9:
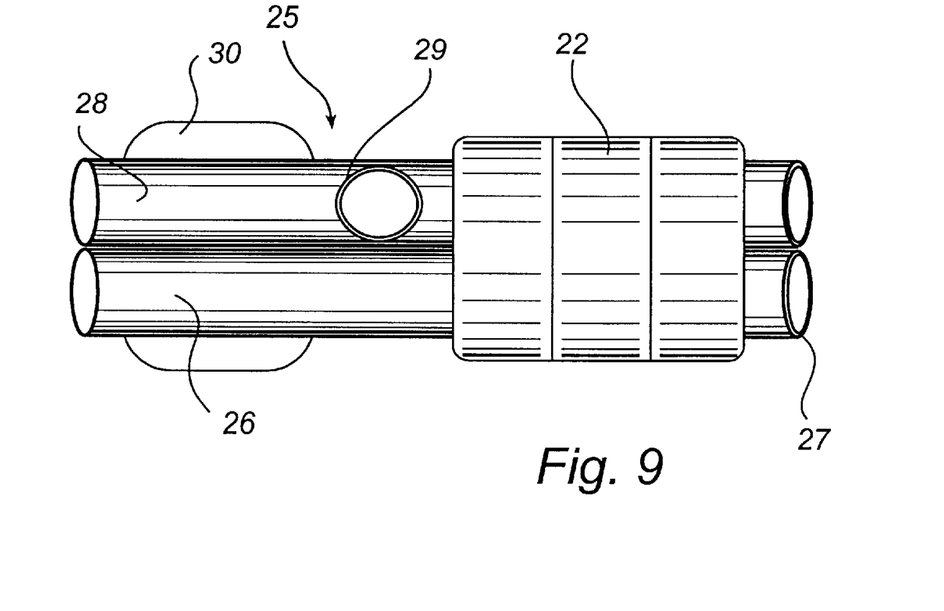
FIG. 9 is a top plan view of a distal part of a first embodiment of a second catheter having two lumens and being designed as an intravenous ultrasound catheter according to the invention for use in a method of bypassing a block in an artery according to the present invention.
Figure 10:
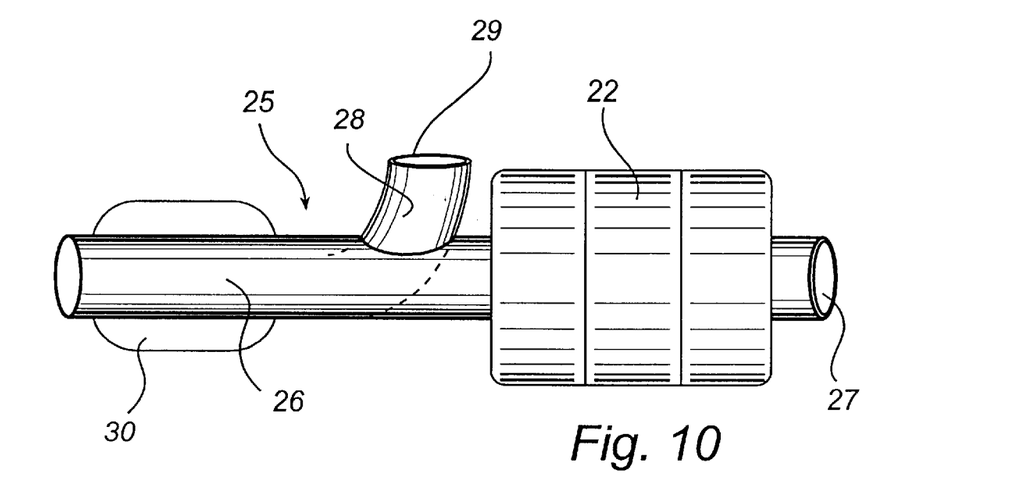
FIG. 10 is an elevation view of the first embodiment of the second catheter shown in FIG. 9.
Figure 11:
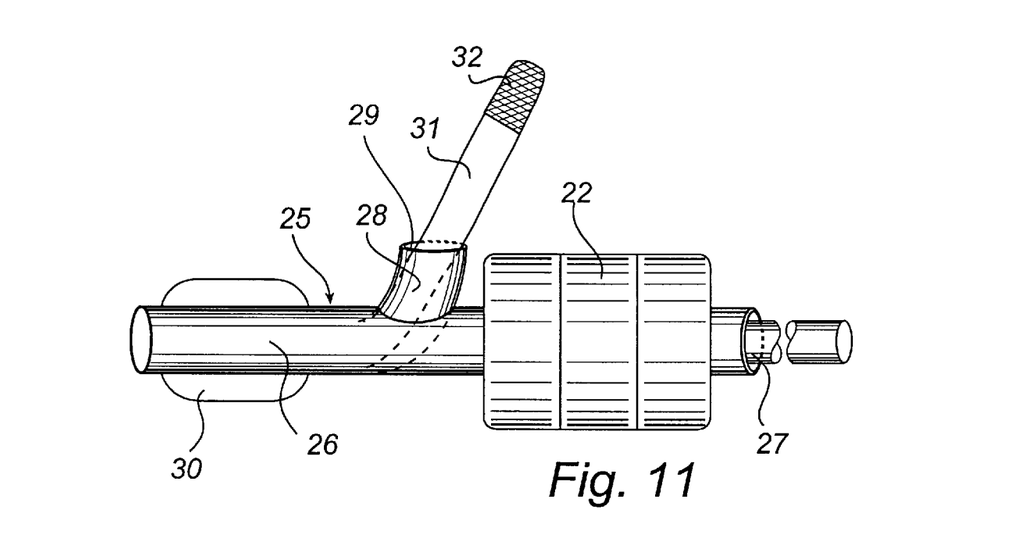
FIG. 11 is an elevation view of the first embodiment of the second catheter shown in FIG. 9 and also illustrates two wires introduced through the lumens thereof.

A first embodiment of the intravenous ultrasound therapeutic catheter 25 is illustrated in FIGS. 9–11. This catheter 25 is a typical angio-graphy catheter of the double lumen type, wherein a first lumen 26 has an axially directed distal opening 27 and a second lumen 28 has a substantially laterally directed distal opening 29. The catheter 25 further has an ultrasound head constituting said detector 22 and being directed substantially in the same lateral direction as the distal opening 29 of the second lumen 28. Finally, the catheter 25 has a balloon 30, whereby its rotational and axial position with a vein may be fixed.

According to the present invention, the intravenous ultrasound therapeutic catheter 25 first is used for making a connection upstream of the block from the arterial catheter 11 positioned in an artery into the vein in which the catheter 25 is introduced. Thus, the ultrasound head or detector 22 of the catheter 25 is used for determining the rotational position of the distal end 12 of the arterial catheter 11. When it is determined that the opening 13 is directly opposite to the vein, this rotational position of the distal end 12 of the arterial catheter 11 is fixed by inflating the balloon 23. Then, the wire 19 having the cutting tip 20 is inserted through the arterial catheter 11 such that the cutting tip 20 will be deflected laterally by the flap 14 out of the lateral opening 13, through the wall of the artery and through the wall of the adjacent vein into this vein.

According to the present invention, the intravenous ultrasound therapeutic catheter 25 is then used for making a connection downstream of the block from the vein in which the catheter 25 is positioned to the same artery from which a connection first was made. Now, the ultrasound head 22 is used to set the rotational position of the catheter 25 such that the opening 29 of the second lumen 28 of the catheter 25 is directly opposite to and thus points toward the artery. The balloon 30 of the catheter 25 is now inflated in order to fix this rotational position of the catheter 25 in the vein. Then, a wire 31 having a cutting tip 32 is inserted through the second lumen 28 of the catheter 25 such that the cutting tip 32 will be deflected laterally out of the distal opening 29 of the second lumen 28, through the wall of the vein and through the wall of the adjacent artery into this artery. The wire 31 is of the same type as the wire 19.

Figure 12:
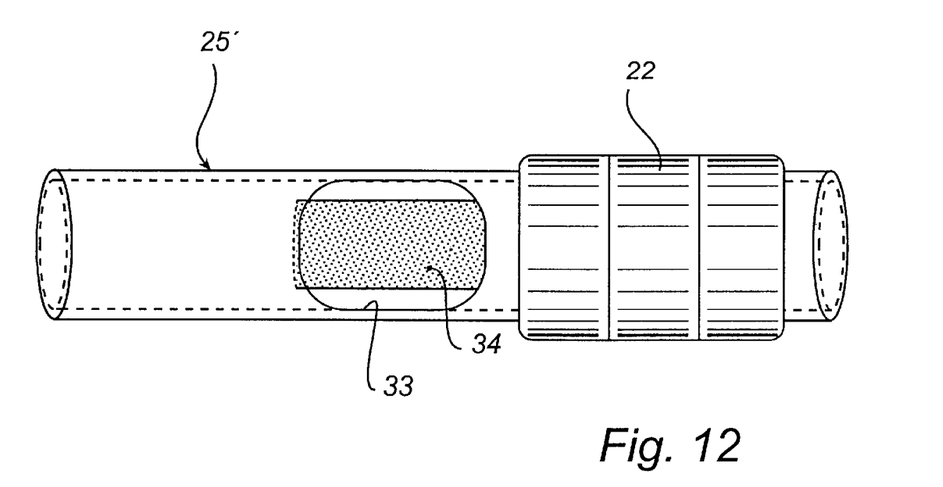
FIG. 12 is a top plan view of a distal part of a second embodiment of a second catheter having a single lumen and being designed as an intravenous ultrasound catheter according to the invention for use in a method of bypassing a block in an artery according to the present invention.
Figure 13:
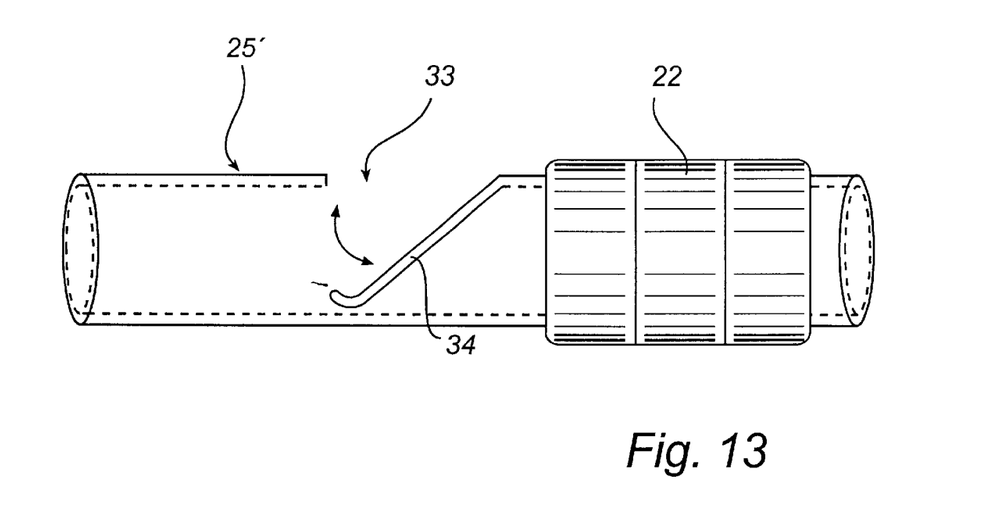
FIG. 13 is a longitudinal sectional view of the second embodiment of the second catheter shown in FIG. 12.

A second embodiment of the intravenous catheter is illustrated in FIGS. 12 and 13. This intravenous ultra-sound therapeutic catheter 25' has the same ultrasound detector 22 as the catheter 25 but is a single lumen catheter, which has a lateral opening 33 and a flap 34. The lateral opening 33 and the flap 34 correspond to the lateral opening 13 and the flap 14 of the first, arterial catheter 11.

When using the intravenous catheter 25', a guide wire is first introduced into the vein and the catheter 25' is then pushed on this guide wire to the area of the block in the artery. During this movement of the catheter 25', the flap 34 is flexed into a position substantially corresponding to the lateral opening 33.

In order to make the connection from the vein into the artery downstream of the block, the guide wire is retracted from the catheter 25' and an active therapeutic wire, i.e. a therapeutic wire having an active tip or end, is introduced from the proximal end of the catheter 25'. When the cutting head of the active wire reaches the flap 34, it is deflected through the lateral opening 33, whereby a connection from the vein and into the artery will be made.

Since the ultrasound transducer 22 of both catheters 25 and 25' is monitoring a sector around the openings 29 and 33, respectively, the movement of the therapeutic wire 31 out of these openings is easily controlled.

Further elements of the instrumentation system according to the present invention are shown in FIGS. 14 and 15, which illustrate a lock mechanism 35 for connecting the ends of two wires, such as the wires 19 and 31, or an active head to the end of a wire, such as the head 20 to the wire 19. The lock mechanism 35 comprises a flexible male member 36 and a female member 37, which are easily connected and disconnected. Of course, many modifications of this lock mechanism are obvious to the man skilled in the art. It should be noted that the lock mechanism 35 does not increase the thickness of the wires 19 and 31 and that the flexibility thereof is hardly affected at all.

Having described embodiments of the arterial catheter and the intravenous catheter as well as their basic functions, a complete description of a method of bypassing a block will now be made, referring to an example illustrated in FIGS. 16–32.

Figure 16:
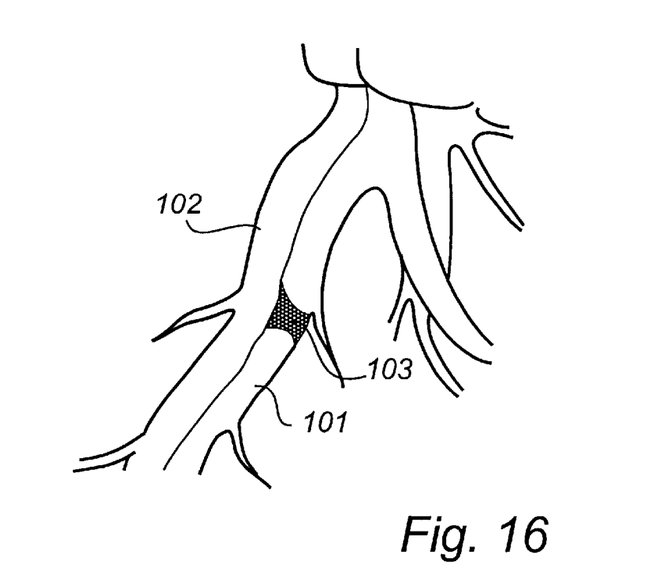
FIGS. 16–32 illustrate the steps performed for positioning a coupling as shown in FIG. 2.

An artery 101 and a parallel vein 102 of a heart are illustrated in FIG. 16. Also, an occlusion or block 103 is shown in the artery 101.

Figures 17, 18, 19, 20:
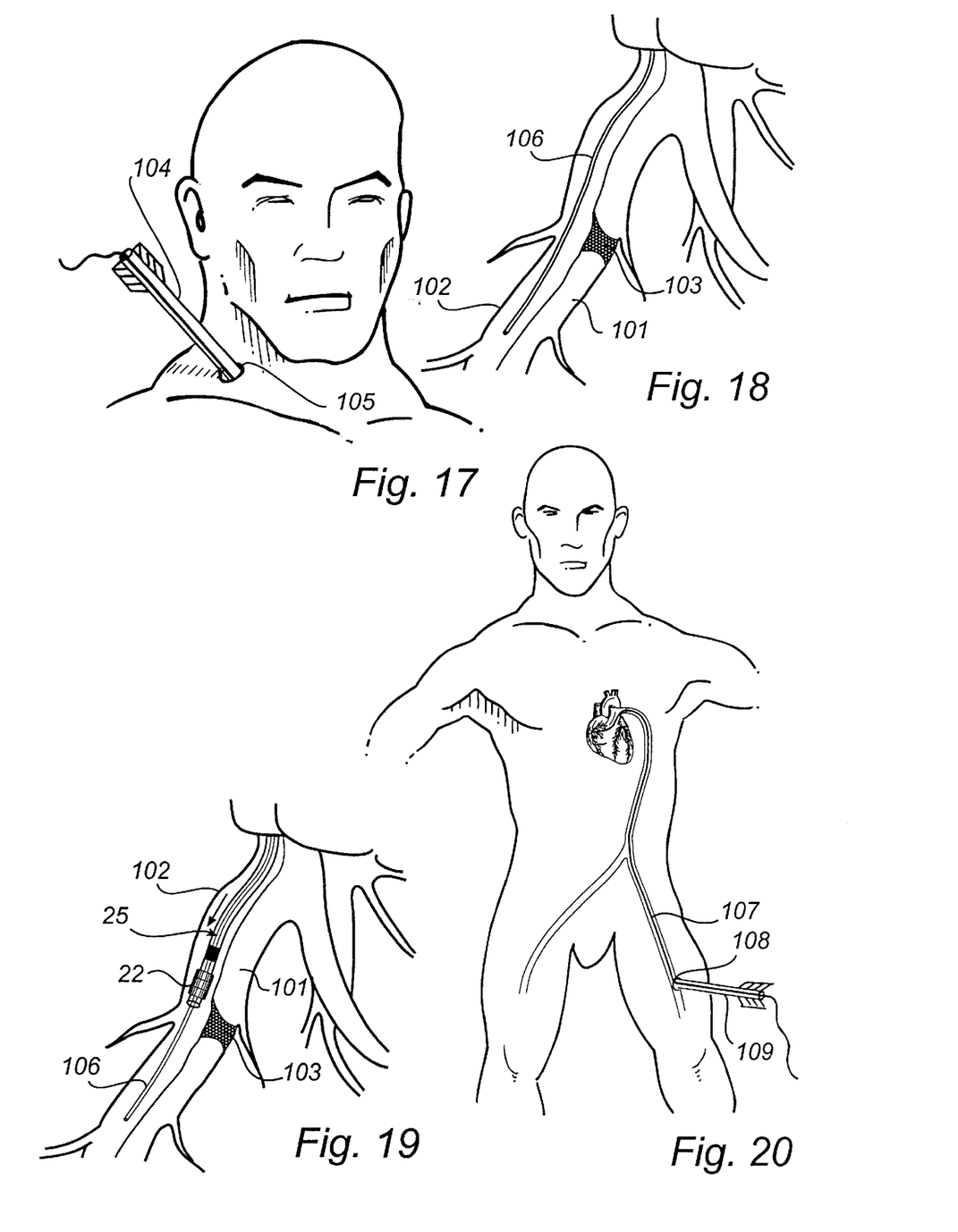

Via a catheter sheet 104 introduced at a puncture site 105 of the jugular vein, as illustrated in FIG. 17, an ordinary guide wire 106 is inserted into the vein 102 past the position of the occlusion in the artery 101, cf. FIG. 18. An intravenous ultrasound therapeutic catheter, such as the catheter 25, is then inserted over this guide wire 106, cf. FIG. 19. The active ultrasound head 22 of the catheter 25 is now used to localize the block 103 in the artery 101.

The information collected by means of the ultrasound head 22 is also used to determine whether the anatomical conditions are good enough for making a coupling according to the present invention.

Figure 21:
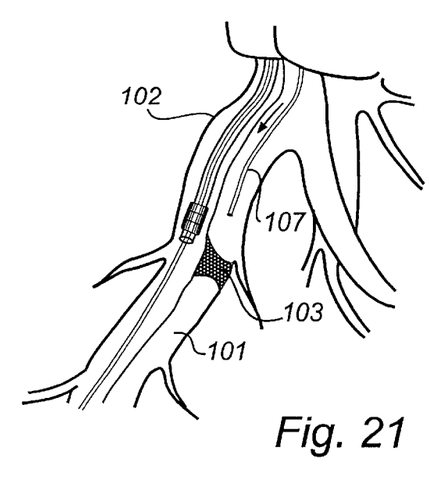
Figure 22:
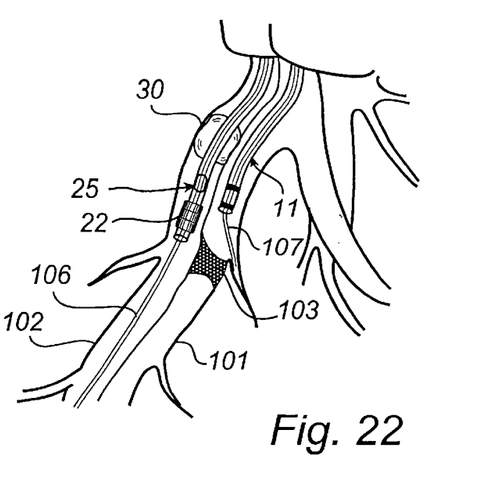
Figure 23:
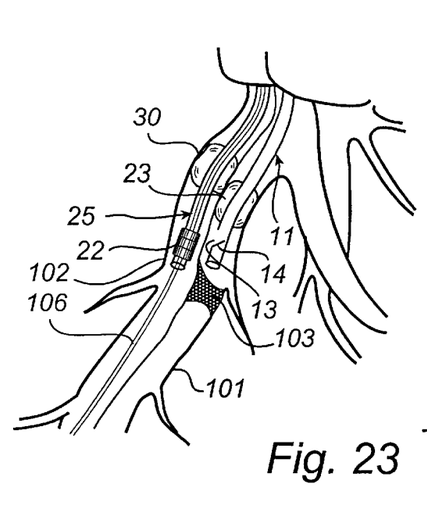

Presuming that acceptable conditions are confirmed, a second common guide wire 107 is now introduced at a puncture site 108 from the femoral artery in the groin (or any other peripheral artery) using a catheter sheet 109 and advanced all the way to the block 103 in the coronary artery 101, cf. FIGS. 20 and 21.

The balloon 30 of the catheter 25 is inflated so as to lock the catheter 25 in a position opposite to the artery 101 and proximal to the block 103. An arterial catheter, such as the catheter 11, is then inserted over this guide wire 107, cf. FIG. 22.

Using the active ultrasound head 22 of the catheter 25 in the vein 102, the reflecting material around the opening 13 at the distal end of the arterial catheter 11 is detected, whereby it is possible to rotate the arterial catheter 11 until its opening 13 is directly facing the vein 102. In this position, the balloon 23 of the catheter 11 is inflated so as to fix the rotational and axial position of the distal part 12 of the arterial catheter 11 in the coronary artery 101. As the next step, the guide wire 107 is retracted whereby the flap 14 returns to its inclined position, cf. FIG. 23.

Figure 24:
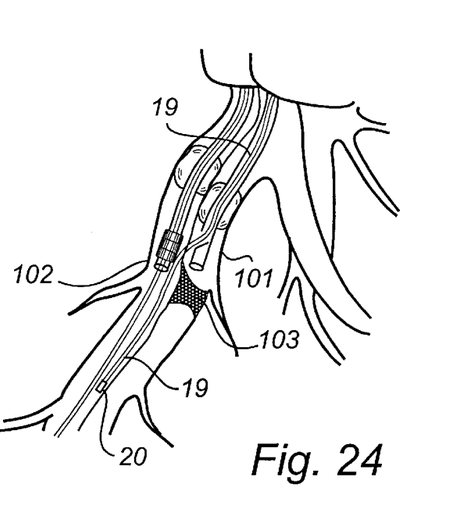

Then, the wire 19 having the cutting tip 20 is inserted through the arterial catheter 11 such that the cutting tip 20 will be deflected laterally by the flap 14 out of the lateral opening 13, and will make a connection through the wall of the artery 101 and through the wall of the adjacent vein 102 into this vein 102, cf. FIG. 24. This movement of the wire 19 and its tip 20 may be monitored by means of the ultrasound head 22 of the catheter 25 in the vein 102. Eventually, the wire 19 extends proximal to the block 103 in the artery 101, via the connection made into the vein 102 and to a position in the vein 102 that is distal to the block 103 in the coronary artery 101.

Figure 25:
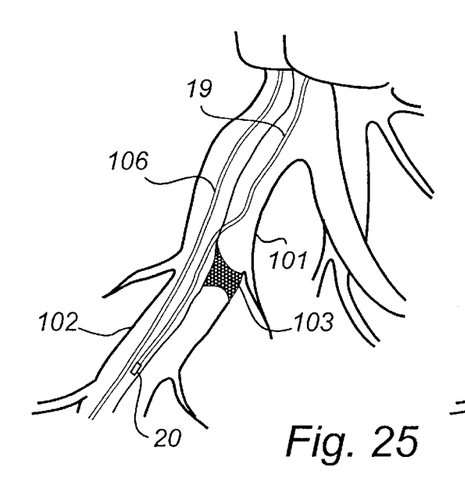

The balloons 23 and 30 may now be deflated and the catheters 11 and 25 withdrawn from the coronary artery 101 and the coronary vein 102, respectively. This is depicted in FIG. 25.

Figure 26:
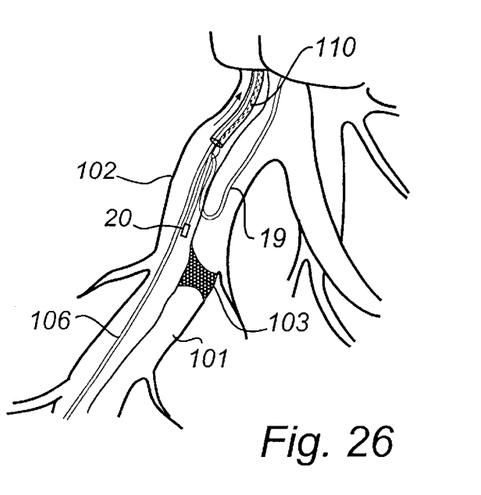
Figure 27:
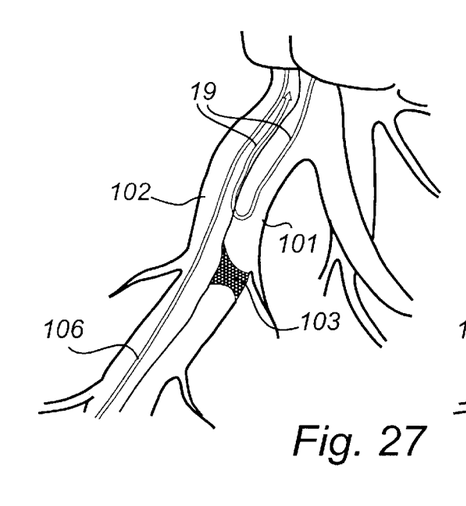
Figure 28:
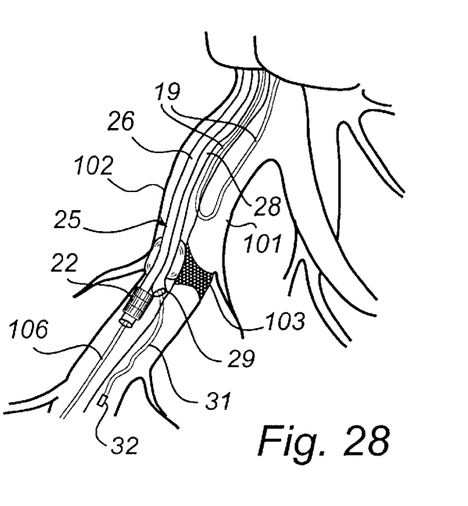

After that, another catheter 110 is introduced over the guide wire 106 to the area of the block 103, where the distal part of the wire 19 is caught and then retracted out of the vein 102 together with the catheter 110, cf. FIG. 26. Thus, the wire 19 now extends from puncture site 108 of the femoral artery in the groin to the block 103 in the coronary artery 101, via the connection through the walls of the coronary artery 101 and the coronary vein 102 into the vein 102 and then back to and out of the puncture site 105 of the jugular vein, cf. FIGS. 27 and 30.

Next, the intravenous ultrasound treatment catheter 25 is again introduced at the puncture site 105 of the jugular vein and is inserted on the guide wire 106 in parallel with the wire 19 to the area of the block 103. After localizing the distal part of the artery 101 by means of the active ultrasound head 22, the balloon 30 will be inflated and the position of the catheter 25 thus fixed. The wire 31 having the cutting head 32 is introduced through the second lumen 28 of the catheter 25. Once it reaches the end of the second lumen 28, it will be deflected out of the lateral opening 29 towards the coronary artery 101 and make a connection through the wall of the coronary vein 102 and the wall of the artery wall 101 into the artery 101, cf. FIG. 28.

Figure 29:
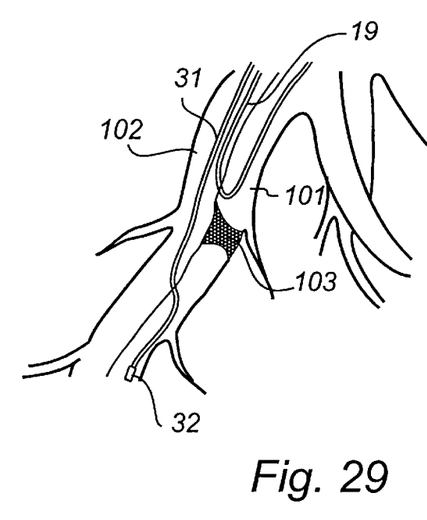
Figure 30:
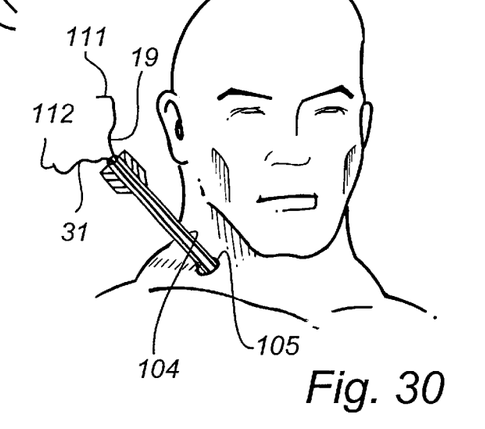
Figure 31:
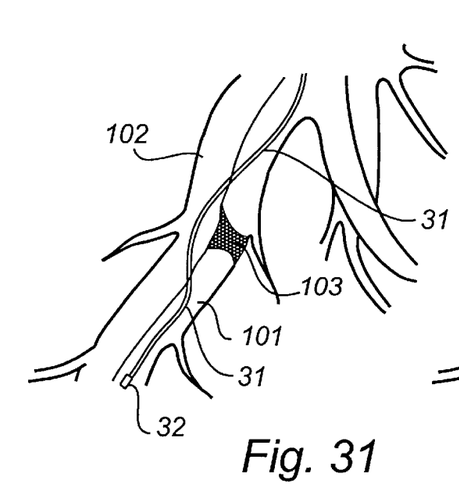
Figure 32:
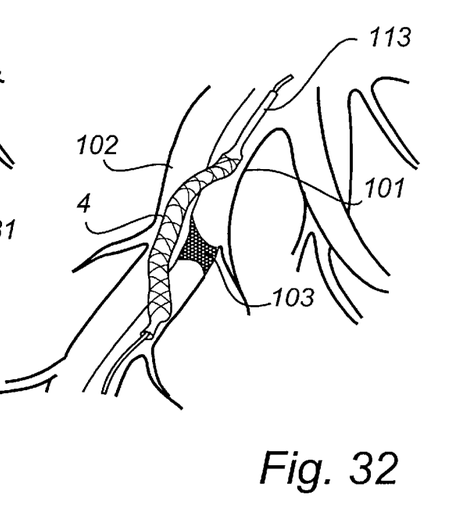

Now, the intravenous ultrasound treatment catheter 25 is retracted from the coronary vein 102, cf. FIG. 29, and the ends 111 and 112 of the wires 19 and 31 outside the puncture site 105 are connected so that they effectively form a single wire 19, 31, cf. FIG. 30. As a result, the wire 19 may be withdrawn from the femoral artery in the groin to such an extent that said single wire 19, 31 extends from the femoral artery in the groin to a point proximally of the block 103 in the coronary artery 101, via the connection through the walls of the coronary artery 101 and the coronary vein 102 into the coronary vein 102, through a part of the coronary vein 102 past the block 103 in the coronary artery 101, via the connection through the walls of the coronary vein 102 and the coronary artery 101 back into the coronary artery 102 distally of the block 103, cf. FIG. 31.

Finally, a covered stent 4, e.g. as described in U.S. patent application Ser. No. 09/461,379, or any other covered stent graft is mounted on a balloon on a catheter 113 and is inserted over the single wire 19, 31 from the femoral artery through the coronary artery 101, through the connection in the walls of the coronary artery 101 and the coronary vein 102 proximally of the block 103, through part of the coronary vein 102, through the connection in the walls of the coronary vein 102 and the coronary artery 101 distally of the block 103, back into the coronary artery distally of the block 103. Now, the proximal end of the covered stent is positioned in the coronary artery 101 proximal to the block 103, and a distal end of the covered stent is positioned in the artery 10l distal to the block 103, cf. FIG. 32.

Finally, the proximal and distal ends 9, 10 of the covered stent 4 are fixed in the coronary artery 101 by inflating said balloon, which is then deflated and withdrawn with the catheter 113. Thereby, the covered stent 4 will bypass the block 103 in the coronary artery 101, as also shown in FIG. 2. It should be noted that since the vein 102 is much wider than the covered stent, i.e. the cross-sectional area of the vein is substantially larger than that of the covered stent (and the coronary artery), the bypass does not obstruct the flow of blood in the coronary vein.

It should be noted that several modifications may be made to the above-described example of the invention. As an example, the catheter 25' may be used instead of the catheter 25. Also, the intravenous catheter 25 or 25' may be used in the artery 1 to make the first connection 6 and thereafter be retracted from the artery and used in the vein 2 as above described. Alternatively, both catheters may be equipped with active ultrasound transducers.

What I claim and desire to secure by Letters Patent is:

1. A method of bypassing a block in an artery which extends along a vein, comprising     forming a first connection between said artery and said vein proximal to the block in the artery,     forming a second connection between said artery and said vein distal to the block in the artery,     introducing a covered stent through said artery proximal to the block therein, through said first connection into said vein, via said vein to and through said second connection, and into said artery distal to the block therein, such that     a proximal end of the covered stent is positioned in the artery proximal to the block therein,     a distal end of the covered stent is positioned in the artery distal to the block therein, and     a part of the covered stent is positioned in the vein such that an effective blood flow through the vein is still allowed, and     fixing the proximal and distal ends of the covered stent within the artery.

2. The method according to claim 1, wherein the step of forming said first connection comprises     introducing a first catheter through the artery, said first catheter having a lateral opening at a distal end thereof,     positioning said lateral opening so as to face said vein proximal to said block,     introducing a first therapeutic wire through said first catheter, said first therapeutic wire having an active distal end, and     advancing the distal end of the first therapeutic wire through the lateral opening of said first catheter, out of the artery and into the vein, thereby forming the first connection.

3. The method according to claim 2, wherein the step of forming the second connection comprises     introducing a second catheter through the vein, said second catheter having a lateral opening at a distal end thereof,     positioning said lateral opening so as to face said artery distal to said block,     introducing a second therapeutic wire through said second catheter, said second therapeutic wire having an active distal end, and     advancing the distal end of the second therapeutic wire through the lateral opening of said second catheter, out of the vein and into the artery distal to said block, thereby forming the second connection.

4. The method according to claim 3, further comprising the step of catching the distal end of the first therapeutic wire and retracting it back through the vein, the first therapeutic wire then extending through the artery proximal to the block, through the first connection and through the vein proximal to the block.

5. The method according to claim 4, wherein the distal end of the first therapeutic wire and the proximal end of the second therapeutic wire are joined to each other outside of the human body and the first therapeutic wire is retracted through the artery, such that the second therapeutic wire extends from the artery distal to the block, through the second connection, via the vein to and through the first connection and into the artery proximal to the block, and finally along the artery proximal of the block.

6. The method according to claim 5, wherein the covered stent is introduced on the second therapeutic wire for bypassing the block.

7. The method according to claim 6, wherein the covered stent is fixed by dilation thereof.

8. The method according to claim 7, wherein the stent is dilated by means of a balloon.

9. The method according to claim 8, further comprising dilating the covered stent along its part in the vein to a diameter which is smaller than the diameter of the vein enclosing part of the covered stent.

10. The method according to claim 2, wherein the positioning of the lateral opening of said first catheter so as to face said vein proximal to said block comprises introducing a detector into the vein for detecting the position of the lateral opening in the first catheter.

11. The method according to claim 10, wherein the detector is used first to detect the position of the block in the artery and then to detect the position of the lateral opening in the first catheter.

12. The method according to claim 10, wherein an ultrasonic transducer is used as position detector and an ultrasound reflecting marking is provided on the first catheter in predetermined relation to the lateral opening at the distal end thereof.

13. The method according to claim 3, wherein the positioning of the lateral opening of said second catheter so as to face said artery distal to said block comprises providing a detector on the second catheter and close to the lateral opening thereof for detecting the position of the artery distal to the block.

14. The method according to claim 2, wherein the positioning of the lateral opening of said first catheter so as to face said vein proximal to said block comprises providing a detector on the first catheter and close to the lateral opening thereof for detecting the position of the vein proximal to the block.

15. The method according to claim 13, wherein an ultrasonic transducer is used as position detector on the second catheter.

16. The method according to claim 14, wherein an ultrasonic transducer is used as position detector on the first catheter.

17. The method according to claim 16, wherein the ultrasonic transducer has the capacity of viewing a limited sector and has the strength to penetrate and depict structures outside the vein and artery, respectively.

18. The method according to claim 16, wherein the ultrasonic transducer has the capacity of viewing 360° around the catheter and has the strength to penetrate and depict structures outside the vein and artery, respectively.

19. The method according to claim 2, wherein the position of said lateral opening of said first catheter facing said vein is fixed by means of a balloon fastening the distal end of the first catheter relative to the artery.

20. The method according to claim 3, wherein the position of said lateral opening of said second catheter facing said artery is fixed by means of a balloon fastening the distal end of the second catheter relative to the vein.

21. A method of bypassing a block in an artery which extends along a vein, comprising
providing a covered stent having a proximal end and a distal end,
positioning the covered stent within said vein having its proximal end introduced into said artery proximal to the block therein and having its distal end introduced into said artery distal to the block therein, the covered stent being positioned within said vein such that an effective blood flow through the vein is still allowed,
connecting the proximal end of the covered stent to the artery proximal to the block, and
connecting the distal end of the covered stent to the artery distal to the block.

22. A catheter system for use in bypassing a block in a human body vessel, comprising
a guiding catheter adapted for introduction into the human body vessel, said catheter comprising:
a distal lateral opening adapted to be positioned proximal to the block in said artery, and
a longitudinal guiding lumen,
wherein said catheter during introduction into the human body vessel has a first configuration in which said lateral opening is essentially blocked and
wherein said catheter when positioned in the human body vessel has a second configuration in which said lateral opening is unblocked and said lumen ends in said lateral opening,
a transfer from the first configuration to the second configuration being controllable by a longitudinal movement of a wire extending through said longitudinal lumen.

23. The catheter system according to claim 22, further comprising a rotational position indicator arranged on the guiding catheter.

24. The catheter system according to claim 23, wherein the rotational position indicator comprises an ultrasound reflecting material at a predetermined position relative to the lateral opening of the guiding catheter.

25. The catheter system according to claim 24, wherein the ultrasound reflecting material at least partly encircles the lateral opening of the guiding catheter.

26. The catheter system according to claim 22, further comprising an inflatable balloon for fixing the distal end of the guiding catheter in the body vessel.

27. The catheter system according to claim 23, further comprising a positioning catheter for introduction into another human body vessel and having a detector responsive to the rotational position indicator.

28. The catheter system according to claim 24, further comprising an ultrasound catheter for introduction into another human body vessel.

29. The catheter system according to claim 28, wherein the ultrasound catheter comprises an ultrasonic transducer for monitoring a positioning of the lateral opening of the guiding catheter when introduced into said body vessel.

30. The catheter system according to claim 29, wherein the ultrasound catheter comprises two parallel lumens, one of which has an axially directed distal opening and the other of which has a laterally directed distal opening.

31. The catheter system according to claim 29, wherein the ultrasonic transducer is directed laterally substantially in the direction of the laterally directed distal opening of the ultrasound catheter.

32. The catheter system according to claim 31, wherein the ultrasonic transducer is positioned distal to the laterally directed opening.

33. The catheter system according to claim 28, further comprising an inflatable balloon for fixing the position of the distal end of the ultrasound catheter in said other body vessel.

34. The method according to claim 15, wherein the ultrasonic transducer has the capacity of viewing a limited sector and has the strength to penetrate and depict structures outside the vein and artery, respectively.

35. The method according to claim 15, wherein the ultrasonic transducer has the capacity of viewing 360° around the catheter and has the strength to penetrate and depict structures outside the vein and artery, respectively.

36. The method according to claim 11, wherein an ultrasonic transducer is used as position detector and an ultrasound reflecting marking is provided on the first catheter in predetermined relation to the lateral opening at the distal end a thereof.

37. The catheter system according to claim 22, wherein said guiding catheter further comprises a distal axial opening and wherein, in said first configuration of the catheter, said longitudinal guiding lumen ends in said axial opening.

38. The catheter system according to claim 22, wherein said guiding catheter further comprises a guide which essentially blocks said lateral opening in the first configuration of the catheter and which is arranged to guide a wire through said lateral opening in the second configuration of the catheter.

39. The catheter system according to claim 22, further comprising a cutting wire having a cutting tip at a distal end thereof, said cutting wire being advancable through the guiding catheter so as to project its cutting tip through the unblocked lateral opening of the guiding catheter.

40. The catheter system according to claim 38, wherein the guide comprises a flap which is hingedly connected at the lateral opening and which has a proximal free end.

41. The catheter system according to claim 40, wherein the flap is moveable between a position essentially blocking the lateral opening of the guiding catheter and a position, wherein the flap is inclined for guiding a wire through said lateral opening.

42. A method of forming a connection between a first and a second human body vessel, said method comprising:

advancing a guiding catheter through the first body vessel to a site where the connection is to be formed, said guiding catheter comprising a longitudinal lumen and a distal lateral opening, said lateral opening being essentially blocked during said advancing, positioning said lateral opening so as to face said second body vessel, transferring the lateral opening to an unblocked state by longitudinal movement of a wire extending through said longitudinal lumen such that the longitudinal lumen ends in the lateral opening, advancing a cutting wire having a cutting tip out through said lateral opening, whereby the cutting wire is directed towards said second body vessel, and further advancing said cutting wire through walls of said first and second body vessels, whereby a connection between the first and the second body vessels is formed.

* * * * *